United States Patent [19]

Gray et al.

[11] Patent Number: 5,176,882
[45] Date of Patent: Jan. 5, 1993

[54] DUAL FIBEROPTIC CELL FOR MULTIPLE SERUM MEASUREMENTS

[75] Inventors: Damien F. Gray, Mountain View; Ganapati R. Mauze; Teddy Kiang, both of Sunnyvale, all of Calif.

[73] Assignee: Hewlett-Packard Company, Palo Alto, Calif.

[21] Appl. No.: 624,020

[22] Filed: Dec. 6, 1990

[51] Int. Cl.⁵ .................. G01N 21/00; A61B 5/00; G01J 1/58
[52] U.S. Cl. ................ 422/82.07; 422/82.06; 422/82.08; 422/82.09; 128/634; 385/12; 250/458.1
[58] Field of Search .............. 422/82.07, 82.04, 82.05, 422/82.08, 52, 82.06, 82.09; 128/634; 350/96.29; 356/39, 417; 250/458.1, 459.1

[56] References Cited

U.S. PATENT DOCUMENTS

| | | | |
|---|---|---|---|
| 4,270,050 | 5/1981 | Brogardh | 250/231.1 |
| 4,476,870 | 10/1984 | Peterson et al. | 128/634 |
| 4,716,363 | 12/1987 | Dukes et al. | 324/77 R |
| 4,785,814 | 11/1988 | Kane | 128/634 |
| 4,800,886 | 1/1989 | Nestor | 128/634 |
| 4,830,013 | 5/1989 | Maxwell | |
| 4,842,783 | 7/1989 | Blaylock | 264/1.4 |
| 4,849,172 | 7/1989 | Yafuso et al. | 422/55 |
| 4,851,195 | 7/1989 | Matthews et al. | 422/68 |
| 4,900,933 | 2/1990 | Nestor et al. | 250/458.1 |
| 5,047,627 | 9/1991 | Yim et al. | 250/227.23 |
| 5,093,266 | 3/1992 | Leader et al. | 422/82.04 |

FOREIGN PATENT DOCUMENTS

0253559A1 1/1988 European Pat. Off.
0336985 10/1989 European Pat. Off. .......... 128/634

OTHER PUBLICATIONS

"A Single-Crystal Ultrasonic Catheter-Tip Velocity Probe," Hartley et al., *Medical Instrumentation* (1974), vol. 8, pp. 241-243, No. 4.

"Subselective Measurement of Coronary Blood Flow Velocity Using a Sterrable Doppler Catheter," Silbey et al., *JACC* (Dec. 1986), vol. 8, No. 6.

"Intravascular Ultrasound: Development and Clinical Potential," Yock et al., *American Journal of Cardiac Imaging*, vol. 2, pp. 185-193, No. 3 (Sep. 1988).

"Similarities and Differences Between Fiber Acoustics and Fiber Optics," C. K. Jen, *IEEE 1985 Ultrasonics Symposium*, Oct. 16-18, 1985.

(List continued on next page.)

*Primary Examiner*—Robert J. Warden
*Assistant Examiner*—Theresa A. Trembley

[57] ABSTRACT

An optical fiber is used in conjunction with a sensor capable of sensing more than one analyte. A first fiber optic sensor cell is used for measuring any combination of ionic species and a second fiber optic sensor cell is used for measuring all gaseous species. In one embodiment, a doped polymer is formed utilizing a hydrophilic polymer which immobilizes a pH sensitive dye and a potassium sensitive fluorescence dye, allowing pH to be measured by detecting the color change of the pH sensitive dye, and the potassium ion concentration to be measured by the change in fluorescence intensity of the potassium sensitive dye. In an alternative embodiment, a doped polymer is formed utilizing a hydrophilic polymer which immobilizes a calcium or sodium ion sensitive fluorescence dye in order to form either a combined pH/calcium sensor or a combined pH/sodium sensor, respectively. Any desired fluorescence dye can be utilized in order to provide detection of a desired analyte or any combination of analytes in conjunction with a pH measurement. A gas sensor is provided utilizing a doped polymer which immobilizes a fluorescence dye sensitive to the gas of interest. In one embodiment, an oxygen sensitive fluorescent dye allows measurement of the partial pressure of oxygen utilizing fluorescence quenching of the oxygen sensitive dye. The concentration of other gases such as nitrous oxide, carbon dioxide, and halogenated anesthetic gases, are measured utilizing infrared absorption within the doped polymer. Each such gas is individually detected utilizing its associated characteristic absorption wavelength.

12 Claims, 2 Drawing Sheets

OTHER PUBLICATIONS

"Review of Intracoronary Doppler Catheters," Craig J. Hartley, *International Journal of Cardiac Imaging* (1989), vol. 4, pp. 159-168.

"Fluorescence Energy Transfer as a Spectroscopic Ruler," L. Stryer. *Ann. Rev. Biochem.*, 47:819-846, 1978.

"Optical Fluorescence and its Application to an Intravascular Blood Gas Monitoring System," Gehrich et al., IEEE (1969), vol. BME-33, No. 2, pp. 117-131.

"Measurements in Medical Practice and Research," Tsitlik et al., Sensors, Jul. 1987, pp. 11-17.

"Fiber-optic diaphragm-curvature pressure transducer," Lawson et al., Optical Society of America, vol. 8, No. 5, pp. 286-288.

"Very High Frequency Pulsed Doppler Apparatus", *Ultrasound in Medicine and Biology*, vol. 15, No. 2, 121-131; (1989), M. Berson, F. Patat, Z. Q. Wange, D. Be and L. Pourcelot.

"Measuring Coronary Blood Flow", *Sensor Technology*, Feb. 1988.

*Doppler Ultrasound and Cardiology*, Liv Hatle, M.D., Bjorn Angelsen, Dr. Techn.

"Synchronized Pulsed Doppler Blood Flow and Ultrasonic Dimension Measurement in Conscious Dogs," *Ultrasound in Medicine and Biology*, vol. 4, pp. 99-110, 1978; C. J. Hartley, H. G. Hanley, R. M. Lewis, and J. S. Cole.

"Pulsed Ultrasonic Doppler Blood-Flow Sensing", Donald W. Baker; *IEEE Transaction on Sonics and Ultrasonics*, vol. 80, SU-17, No. 3, Jul. 1970.

"A New Doppler Flowmeter System and its Operation with Catheter Mounted Transducers," *Cardiovascular Applications of Ultrasound*, Robert S. Reneman, Edit North-hollond/Amrican Eleseuir Publishers J. M. Reid, D. L. Davis, H. J. Rickets and M. P. Spencer.

DUAL FIBEROPTIC CELL FOR MULTIPLE SERUM MEASUREMENTS

BACKGROUND OF THE INVENTION

This invention pertains to in vivo physiological sensors, and more particularly in vivo physiological sensors utilizing optical fibers and capable of measuring a plurality of serum analytes.

DESCRIPTION OF THE PRIOR ART

It is well known in the prior art to measure certain parameters in a blood stream, such as pH and concentrations of $O_2$, $CO_2$, $Na+$, and $K+$. When monitoring a patient, it is necessary to make frequent determinations of these analytes, and thus determinations of these analytes is often made in vivo.

It is known in the prior art to utilize a plurality of sensors, one for each analyte such that the sensor is placed in a patient's blood stream and electrical signals detected which are indicative of the relative concentration of the analyte being measured. However, if it is desired to measure a plurality of analytes, the use of a plurality of sensors is required, with the attendant discomfort to the patient and complexity of the electronic monitoring apparatus.

European patent application 0 253 559 A1 describes an apparatus and method for making in vivo measurements of $CO_2$ concentration in a patient's blood stream. This structure utilizes an optical fiber which transmits an infrared signal to the distal end of the optical fiber, whereupon it is reflected. The optical fiber is permeable to $CO_2$, and thus the intensity of the return signal is diminished in proportion to the concentration of the $CO_2$ in the optical fiber. Thus, the change in intensity of the infrared light is indicative of the $CO_2$ concentration in the patient's blood.

"Optical Fluorescence and Its Application to an Intravascular Blood Gas Monitoring System," Gehrich et al., IEEE Transactions on Biomedical Engineering, Volume BME-33, NO. 2, February 1986, pages 117-132, describes the use of optical fluorescence to measure pH, $PCO_2$, and $PO_2$ utilizing appropriate dyes. A single intravascular blood gas probe includes three optical fibers terminating in a pH, $PCO_2$, and $PO_2$ sensor, respectively. Each fluorescent dye emits energy at a wavelength different from that at which it absorbs the excitation energy, allowing a single optical fiber to both deliver excitation energy to the dye and receive energy emitted by the dye. By detecting the amount of emitted energy, the absorbed energy is determined, which in turn is related to the analyte being measured.

The greatest difficulty in designing in vivo physiological sensors, including those utilizing optical fibers, is the limitation on physical dimension. On the one hand, the diameter of the individual optical fibers must be sufficiently large to allow the transmission of sufficient optical signal to permit accurate measurements to be made. On the other hand, the total diameter of the physiological sensor must be sufficiently small to minimize the opening in the patient at the measurement site in order to avoid adding risk to the patient being monitored, as well as to minimize the discomfort of the patient. Due to these limitations, there is a limit to the number of analytes which can be monitored simultaneously by a single physiological sensor since, as taught by the prior art, a physiological sensor must include one optical fiber for each analyte to be measured.

There remains the need, therefore, to provide a physiological sensor capable of measuring a plurality of analytes substantially simultaneously and yet which is small in size.

SUMMARY OF THE INVENTION

In accordance with the teachings of this invention, a physiological sensor is provided in which an optical fiber is used in conjunction with a sensor capable of sensing more than one analyte. In one embodiment to this invention, a first fiber optic sensor cell is used for measuring any combination of ionic species and a second fiber optic sensor cell is used for measuring all gaseous species. In this manner, the number of analytes which may be monitored utilizing a single sensor is increased as compared with the prior art.

In one embodiment of this invention, a doped polymer is formed utilizing a hydrophilic polymer which immobilizes a pH sensitive dye and a potassium sensitive fluorescence dye, allowing pH to be measured by detecting the color change of the pH sensitive dye, and the potassium ion concentration to be measured by the change in fluorescence intensity of the potassium sensitive dye.

In an alternative embodiment, a doped polymer is formed utilizing a hydrophilic polymer which immobilizes a calcium or sodium ion sensitive fluorescence dye in order to form either a combined pH/calcium sensor or a combined pH/sodium sensor, respectively. In accordance with the teachings of this invention, any desired fluorescence dye can be utilized in order to provide detection of a desired analyte or any combination of analytes in conjunction with a pH measurement.

A gas sensor is provided utilizing a doped polymer which immobilizes a fluorescence dye sensitive to the gas of interest. In one embodiment, an oxygen sensitive fluorescent dye is used to allow measurement of the partial pressure of oxygen utilizing fluorescence quenching of the oxygen sensitive dye. The concentration of other gases such as nitrous oxide, carbon dioxide, and halogenated anesthetic gases, are measured utilizing infrared absorption within the doped polymer. Each such gas is individually detected utilizing its associated characteristic absorption wavelength.

DETAILED DESCRIPTION

Figure 1:
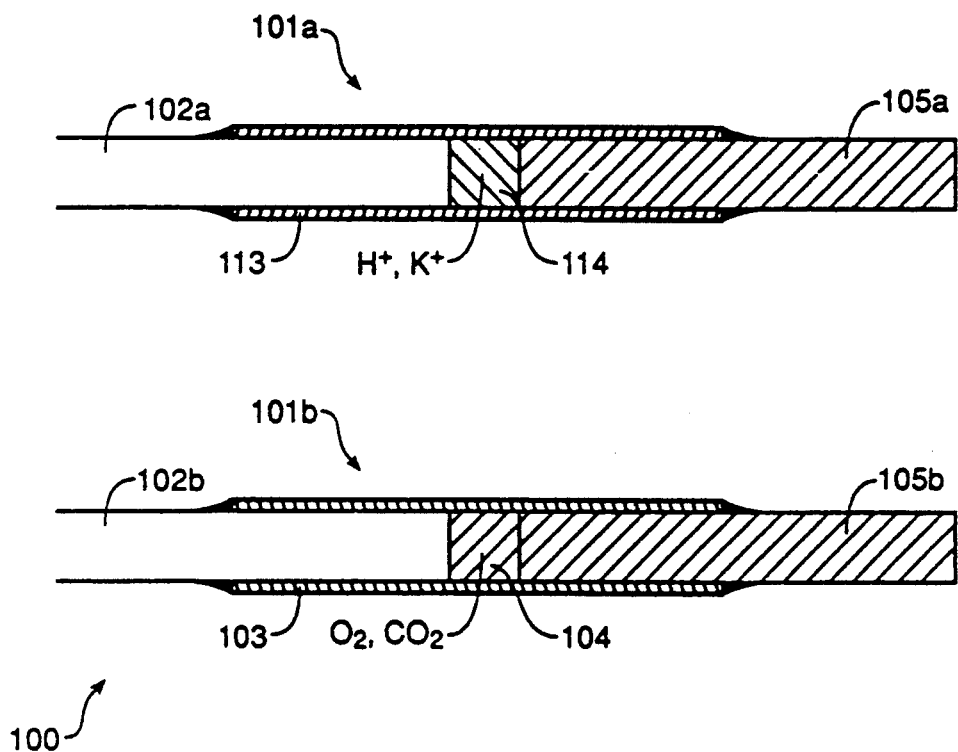
FIG. 1 is a diagram depicting one embodiment of a dual fiber optic cell for multiple serum measurements constructing in accordance with the teachings of this invention.

In accordance with the teachings of this invention, a physiological sensor 100, shown in FIG. 1, is provided which utilizes only two optical fiber sensors 101a, 101b, to make measurements on all clinically important analytes such as blood gases (pH, oxygen, and carbon dioxide), electrolytes (potassium ion, calcium ion, and sodium ion, etc.) and anesthetic gases (nitrous oxide, halothane, enflurane, isoflurane, etc.). As shown in FIG. 1, physiological sensor 100 includes a first fiber optic sensor cell 101a for measuring any combination of ionic species and a second fiber optic sensor cell 101b for measuring all gaseous species. By utilizing one sensor to measure ionic species, and another fiber optic sensor for measuring gaseous species, the number of analytes which may be monitored utilizing a single sensor is greatly increased as compared with the prior art, while providing a physiological sensor of small diameter since only two optical fibers are necessary.

Ionic sensor cell 101a includes optical fiber 102a whose proximal end (not shown) is connected to a suitable source of excitation energy and suitable detection apparatus, as is described in more detail later. An ion permeable membrane 113 serves to house optical fiber 102a, reflector 105a, and polymer 114. Energy transmitted from the source (not shown) is communicated via optical fiber 102a through doped polymer 114, to the face of reflector 105a. The energy is then reflected by reflector 105a back through doped polymer 114 to optical fiber 102a for the return trip to the optical sensor mechanism. Reflector 105a may conveniently be formed utilizing stainless steel or the like. Doped polymer 114 comprises a hydrophilic polymer which immobilizes a pH sensitive dye and a potassium sensitive dye. In one embodiment, for example, the hydrophilic polymer comprises polyacrylamide or polyhydroxyethyl methacrylate, the pH sensitive dye comprises phenol red. pH is measured by detecting the color change of the pH sensitive dye, in a well known manner. Potassium ion concentration is measured by the change in fluorescence intensity of the potassium sensitive dye due to its interaction with the chelating reagent (such as crown ether, valinomycin, or the like) attached to the dye.

Of importance, measurement of both pH and potassium concentration are made utilizing a single optical fiber 102a since each such measurement requires the detection of a different part of the visible light spectrum Thus, optical fiber 102a receives two different excitation wavelengths by alternating the selection of light sources coupled to optical fiber 102a, and detector means serves to detect two different corresponding emission wavelengths.

In an alternative embodiment, doped polymer 114 includes calcium or sodium ion sensitive fluorescence dye which is used in a similar manner to form fiber optic sensor 101a as either a combined pH/calcium sensor or a combined pH/sodium sensor, respectively. In a similar fashion, doped polymer 114 can include any desired fluorescence dye in order to enable fiber optic sensor 101a to measure any desired serum electrolyte in combination with pH measurement. For example, the following table specifies possible fluorescent chromophores for sensing various types of ions.

| FLUORESCENT CHROMOPHORES FOR ION SENSING | | | |
|---|---|---|---|
| Ion | Chromophore | Excitation Wavelength (nm) | Emission Wavelength (nm) |
| K⁻ | N-(9.Anthryl-methyl)Monoaza-18-crown-6 | 366–370 | 412–416 |
| K⁻ | Coumaro Cryptand of Kryptofix 222 | 330 | 340–500 |
| Na⁻ | Coumaro Cryptand of Kryptofix 221 | 330 | 340–500 |
| Li⁻ | Coumaro Cryptand of Kryptofix 211 in the presence of Kryptofix 221 | 330 | 340–500 |
| H⁻ | Hydroxipyrene | 460 | 520 |

| -continued | | | |
|---|---|---|---|
| FLUORESCENT CHROMOPHORES FOR ION SENSING | | | |
| Ion | Chromophore | Excitation Wavelength (nm) | Emission Wavelength (nm) |
| | trisulfonic acid | | |

Ion permeable membrane 113 comprises, for example, cuprophan and serves to allow the ions of interest to travel between the fluid being measured and doped polymer 114.

Also shown in FIG. 1 as part of physiological sensor 100 is gas sensor 101b. Gas sensor 101b includes optical fiber 102b having its proximal end (not shown) connected to receive appropriate excitation energy and to detector means for detecting the response to such excitation energy from sensor 101b. This excitation energy is passed through doped polymer 104, to reflector 105b, whereupon it is reflected back through doped polymer 104 and into optical fiber 102b for transmission to the detecting device. Reflector 105 is conveniently made of stainless steel, for example. Gas permeable membrane 103 serves to allow gas to travel between doped polymer 104 and the fluid being measured. Gas permeable membrane 103 comprises, for example, silicone rubber. Doped polymer 104 is, for example, a hydrophobic polymer which is gas permeable.

Doped polymer 104 comprises, for example, silicon rubber or its derivatives which immobilizes an oxygen sensitive fluorescence dye. The partial pressure of oxygen in the fluid being measured can be determined by fluorescence quenching of the immobilized dye, as is well known in the art. Fluorescent dyes suitable for use in doped polymer 104 for the detection of oxygen are shown in the following table.

| FLUORESCENT DYES FOR OXYGEN SENSING | | |
|---|---|---|
| Dye | Excitation Wavelength (nm) | Emission Wavelength (nm) |
| Platinum tetra (penta phenyl porphyrine) | 480–600 | 620 |
| 9,10 Diphenyl Anthracene | 350–400 | 410–434 |
| Pyrenebutyric acid | 300–350 | 395 |
| Tris(4,7 diphenyl 1,10 phenanthroline) Ruthenium(II) Perchlorate | 337 | 450 |

Other gases that are of clinical importance such as nitrous oxide, carbon dioxide, and halogenated anesthetic gases are measured using gas sensor cell 101b via optical fiber 102b utilizing infrared absorption within doped polymer 104. Of importance, each such gas is individually detected since each gas has associated therewith its own characteristic absorption wavelength which can be individually measured. If desired, multiple absorption wavelengths may be utilized to determine the concentration of a single or multiple gases using multi variant analysis, such as singular value decomposition (SVD) or similar techniques. For example, the major absorption bands of a number of such gases of clinical interest are shown in the following table.

| MAJOR ABSORPTION BANDS OF CLINICALLY IMPORTANT GASES | |
|---|---|
| Gas | Major Absorption Bands (microns) |
| Carbon Dioxide | 4.3, 2.74, 2.67, 2.03, 1.98, 1.93 |
| Nitrous Oxide | 5.3, 4.5, 4.23, 4.04, 3.90, 3.53, 2.94, 2.84, 2.64, 2.58, 2.23, 2.08 |
| Isoflurane | 2.15–4.72, 1.62–1.92, 1.37, 1.12 |
| Enflurane | 2.15–4.72, 1.62–1.92, 1.37, 1.12 |
| Halothane | 2.24–4.7, 1.63–1.86, 1.39, 1.12 |
| Water | 4.18–4.31, 2.54–2.78 |

As will be appreciated by those of ordinary skill in light of the teachings of this invention, many minor absorption bands of these species are available for use as well. Furthermore, other species of interest can be detected in a similar fashion utilizing appropriate absorption bands. Absorption bands have widely varying widths and shapes which can, if desired, be put to use during the detection process.

Figure 2:
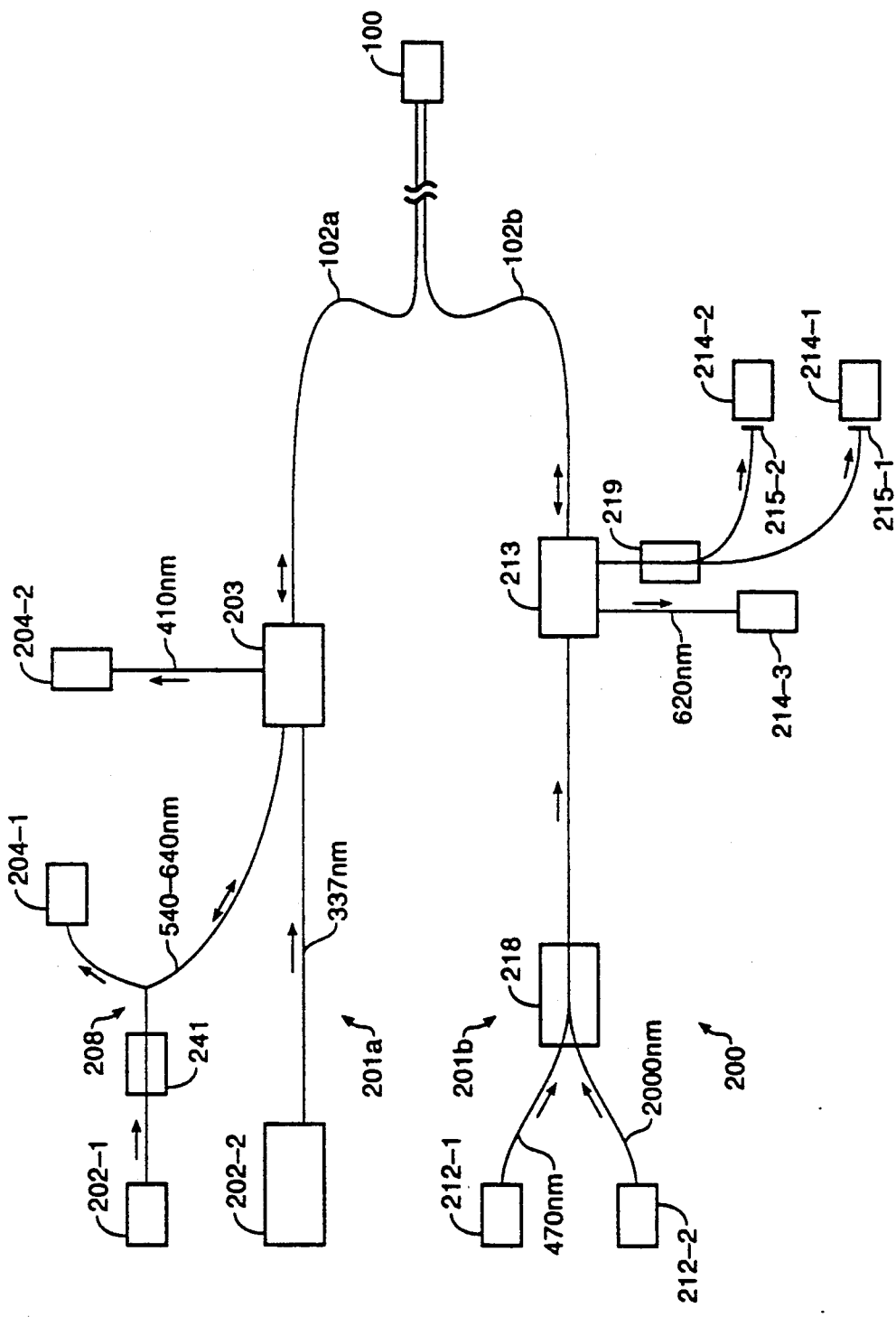
FIG. 2 is a diagram depicting a measurement system including sources of excitation energy, detector means, and the physiological sensor of this invention.

FIG. 2 depicts a block diagram of one embodiment of a system constructed in accordance with the teachings of this invention. System 200 includes physiological sensor 100 and optical fibers 102a and 102b of FIG. 1. In the embodiment of FIG. 2, the ion sensor uses a potassium specific fluorescent dye which absorbs at 330 nm and emits at 410 nm. The pH is measured by the absorption of phenol red at 547 nm. The ion sensor is referenced utilizing a red LED emitting at 650 nm in order to provide a reference measurement to determine losses due to optical fiber bending, connectors, etc.

In this embodiment, LED 202-1 is a red/green LED which is coupled to an optical fiber. Red/green light in the fiber is then mode scrambled by mode scrambler 241 to reduce differences in the reference and signal arms. The output signal from mode scrambler 241 is then coupled by Y-piece multiplexor 208, and in turn is input to wavelength division multiplexor 203. Laser 202-2 comprises an $N_2$ laser providing uv energy at approximately 337 nm to wavelength division multiplexor 203. Wavelength division multiplexor 203 thus provides red/green/uv light to optical fiber 102a which travels to the ion sensor portion of physiological sensor 100. There, the uv light excites fluorescence in the potassium specific dye, a portion of the green light is absorbed by the phenol red, and the red light is merely reflected.

The fluorescence light and the reflected green and red light travel back through optical fiber 102a to wavelength division multiplexor 203, where they are split into short and long wavelength components, with a split occurring at approximately 500 nm. The short wavelength blue light which was produced by fluorescence from the potassium specific dye is coupled to silicon photodiode 204-2 for detection, from which the potassium concentration is derived. The long wavelength light is coupled back through Y-piece multiplexor 208 into silicon photodiode 204-1. The red and green portions of red/green LED 202-1 are time division multiplexed in order to alternately provide red and green reflected light to silicon photodiode 204-1 so that red and green light are detected individually. The reflected red light is used for calibration purposes to account for losses in the system due to connectors, bends, and the like. The detection of the green light provides an indication of the potassium content of the fluid being measured by physiological sensor 100.

In the embodiment of FIG. 2, the gas sensor portion of physiological detector 100 utilizes an oxygen sensitive fluorescent dye which absorbs at 470 nm and emits at 620 nm. The carbon dioxide concentration of the fluid being measured by physiological sensor 100 is determined by absorption at 2 microns. In one embodiment, the fluorescent sensor uses a phase dependent technique as described in U.S. Pat. No. 4,716,363 on an invention entitled "Exponential Decay of Time Constant Measurement Using Frequency of Offset Phase-locked Loop: System and Method" which is assigned to Hewlett-Packard Company, the assignee of this application. This technique precludes the need for the use of a reference wavelength such as the red light used in the ion sensor portion of this embodiment. The carbon dioxide measurement is referenced from the zero absorption level located adjacent to the $CO_2$ peak at 2 microns.

Referring to FIG. 2, LED 212-1 provides light at 470 nm and LED 212-2 provides light at 2 microns. This light from LEDs 212-1 and 212-2 are combined in fused taper coupler 218 and then applied to wavelength division multiplexor 213. This light is coupled by wavelength division multiplexor 213 to optical fiber 102b. A portion of the 2 micron light is absorbed by the $CO_2$ within physiological sensor 100, and the remainder is reflected. The light from the LEDs outside the $CO_2$ absorption bands is reflected and acts as a reference. The 470 nm light energy excites fluorescence in the oxygen sensitive fluorescent dye contained within physiological sensor 100. The red fluorescence light is coupled back into optical fiber 102b. The light returning from physiological sensor 100 via optical fiber 102b is split by wavelength division multiplexor 213, with the red 620 nm light being directed to silicon avalanche photodiode 214-3 for detection in order to provide an indication of the oxygen concentration detected by physiological sensor 100. The returning light within the region of approximately 2 micron is split by fused taper coupler 219 and directed through background filter 215-1 (passing 2110 nm) to infrared detector 214-1, and signal filter 215-2 (passing 2019 nm) to IR signal detector 214-2. Signal detector 214-2 serves to provide an indication of the carbon dioxide concentration measured by physiological sensor 100, as adjusted by the amount of background light which is detected by background detector 214-1. The pass bands of the background and signal filters are dependent on the polymer used (silicone rubber in the above example).

The following parts list is indicative of the type of components which may be used to construct the embodiment depicted in FIG. 2.

| Component from FIG. 2 | Component |
|---|---|
| red/green LED 202-1 | Hewlett-Packard HPMP-4000 |
| $N_2$ laser 202-2 | Laser Science, Inc. Cambridge, MA model VSL-337ND |
| Y-piece multiplexor 208 | German utility model number G-86-07-002.9 granted on October 19, 1989 |
| Silicon photodiode 204-1, 204-2 | RCA C30971EL |
| Wavelength division multiplexor 203, 213 | Custom made using grin lens or bulk optics |
| 470 nm LED 212-1 | Siemens SiC blue LED |
| 2000 nm LED 212-2 | Laser Monitoring Systems, Ltd. GaSb LED |
| Silicon avalanche | RCA C30952FL |

| Component from FIG. 2 | Component |
|---|---|
| photodiode 214-3 Splitter | Fused taper coupler available from Canstar |
| IR detectors 214-1, 214-2 | Epitaxx ETX-300 GR2.2 |
| Signal filters 215-1, 215-2 | Available from Optical Coating Laboratories, Inc. of Santa Rosa, CA and Corion of Holliston, MA. |

All publications and patent application cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit of scope of the appended claims.

What is claimed is:

1. A physiological sensor comprising:
   a sample region for containing a sample including one or more sets of analytes to be determined, each set of analytes including one or more analytes to be determined;
   a hydrophilic member located within said sample region;
   means for coupling first input energy to said hydrophilic member;
   means for coupling first output energy from said hydrophilic member to a detector; p1 means for causing at least some of said first input energy to be coupled as returning energy to said means for coupling first output energy from said hydrophilic member after passing through a sample, the amount of said returning energy being indicative of pH within said sample region;
   dopants contained within said hydrophilic member serving to cause florescence in response to at least some of said first input energy, as a function of one or more analytes of a second set of analytes comprising the set of analytes consisting of one or more ions other than pH, within said sample region;
   a hydrophobic member located within said sample region;
   means for coupling second input energy to said hydrophobic member;
   means for coupling second output energy from said hydrophobic member to a detector;
   means for causing at least some of said second input energy to be coupled as returning energy to said means for coupling second output energy from said hydrophobic member after passing through a sample, the amount of said returning energy being indicative of a third set of analytes comprising the set of analytes consisting of one or more gasses other than oxygen; and
   dopants contained within said hydrophobilic member serving to cause fluorescence in response to at least some of said second input energy, as a function of oxygen within said sample region.

2. A physiological sensor as in claim 1 wherein said sample region is housed, at least partially, by a membrane which is permeable by said analytes.

3. A physiological sensor as in claim 1 wherein said one or more gases are selected from the group of gases consisting of nitrous oxide, carbon dioxide, and halogenated anesthetic gases.

4. A physiological sensor as in claim 1 wherein said second input energy comprises wavelengths corresponding to one or more characteristic absorption wavelengths of said one or more gases.

5. A physiological sensor as in claim 1 wherein:
   said first and second input energy is broadband and covers the region of interest;
   said first and second output energy is spectrally separated from said first and second input energy; and
   said physiologically sensor further comprises means for analyzing said first and second output energy by multivariant analysis to determine said one or more sets of analytes.

6. A physiological sensor as in claim 5 wherein said means for analyzing said first and second output energy comprises means for analyzing said first and second output energy utilizing singular value decomposition.

7. A physiological sensor as in claim 1 wherein said one or more types of ions are selected from the group of ions consisting of hydrogen, potassium, sodium, calcium, and lithium.

8. An instrument for sensing one or more analytes in a sample comprising:
   a sample region for containing a sample including one or more sets of analytes to be determined, each set of analytes including one or more analytes to be determined;
   means for providing input energy having a plurality of wavelengths, at least one of said wavelengths corresponding to an associated one of said analytes;
   a detector for detecting energy provided by said sample in response to said input energy;
   a hydrophilic member located within said sample region;
   means for coupling first input energy to said hydrophilic member;
   mean for coupling first output energy from said hydrophilic member to said detector;
   means for causing at least some of said first input energy to be coupled as returning energy to said means for coupling first output energy from said hydrophilic member after passing through said sample, the amount of said returning energy being indicative of pH within said sample region;
   dopants serving to cause fluorescence in response to at least some of said first input energy, as a function of one or more analytes of a second set of analytes comprising the set of analytes consisting of one or more ions other than pH, within said sample region;
   a hydrophobic member located within said sample region;
   means for coupling second input energy to said hydrophobic member;
   means for coupling second output energy from said hydrophobic member to a detector;
   means for causing at least some of said second input energy to be coupled as returning energy to said means for coupling second output energy from said hydrophobic member after passing through said sample, the amount of said returning energy being indicative of a third set of analytes comprising the set of analytes consisting of one or more gasses other than oxygen: and dopants serving to cause fluorescence in response to at least some of said second input energy, as a function of oxygen within said sample region.

9. An instrument as in claim 8 wherein said sample region is housed. at least partially, by a membrane which is permeable by said analytes.

10. An instrument as in claim 8, wherein said one or more gases are selected from the group of gases consisting of oxygen. nitrous oxide. carbon dioxide. and halogenated anesthetic gases.

11. An instrument as in claim 8 wherein said input energy comprises wavelengths corresponding to one or more characteristic absorption wavelengths of said one or more gases.

12. An instrument as in claim 8 wherein said one or more types of ions are selected from the group of ions consisting of hydrogen, potassium. sodium, calcium, and lithium.

* * * * *